(12) United States Patent
Morad et al.

(10) Patent No.: US 10,471,446 B2
(45) Date of Patent: Nov. 12, 2019

(54) ENHANCING STABILITY AND THROUGHPUT OF AN ELECTROHYDRODYNAMIC SPRAY

(71) Applicants: Mohammad Reza Morad, Tehran (IR); Alireza Rajabi, Tehran (IR); Seyed Rahman Pejman Sereshkeh, Tehran (IR); Maryam Razavi, Tehran (IR); Saeed Jowkar, Tehran (IR); Nina Rahbari, Tehran (IR)

(72) Inventors: Mohammad Reza Morad, Tehran (IR); Alireza Rajabi, Tehran (IR); Seyed Rahman Pejman Sereshkeh, Tehran (IR); Maryam Razavi, Tehran (IR); Saeed Jowkar, Tehran (IR); Nina Rahbari, Tehran (IR)

( * ) Notice: Subject to any disclaimer, the term of this patent is extended or adjusted under 35 U.S.C. 154(b) by 344 days.

(21) Appl. No.: 15/430,496

(22) Filed: Feb. 12, 2017

(65) Prior Publication Data

US 2017/0151578 A1 Jun. 1, 2017

Related U.S. Application Data

(60) Provisional application No. 62/304,246, filed on Mar. 6, 2016.

(51) Int. Cl.
*B05B 5/025* (2006.01)
*H01J 49/16* (2006.01)
*G01N 30/72* (2006.01)

(52) U.S. Cl.
CPC ....... *B05B 5/0255* (2013.01); *G01N 30/7266* (2013.01); *H01J 49/167* (2013.01)

(58) Field of Classification Search
CPC .. H01J 49/0431; H01J 49/0445; H01J 49/165; H01J 49/167; G01N 30/7266; B05B 5/0255
USPC .................................. 250/288; 204/451, 601
See application file for complete search history.

(56) References Cited

U.S. PATENT DOCUMENTS

| 6,297,499 | B1 | 10/2001 | Fenn | |
|---|---|---|---|---|
| 6,723,985 | B2 | 4/2004 | Schultz et al. | |
| 7,858,932 | B2 * | 12/2010 | Finch | H01J 49/167 250/282 |
| 8,153,992 | B2 * | 4/2012 | Horiike | B05B 5/057 250/288 |
| 8,794,551 | B2 | 8/2014 | Gomez | |

(Continued)

FOREIGN PATENT DOCUMENTS

| KR | 101235865 B1 | 2/2013 |
|---|---|---|
| WO | 2006047453 A2 | 5/2006 |

OTHER PUBLICATIONS

Joon Sang Kang, Free-surface electrospray technique using a multi-hole array, Journal of Aerosol Science, Aug. 2012, vol. 55, pp. 25-30.

*Primary Examiner* — Darren W Gorman
(74) *Attorney, Agent, or Firm* — Bajwa IP Law Firm; Haris Zaheer Bajwa

(57) ABSTRACT

Disclosed herein is an emitting device for an electrospray system. The emitting device may include a surface extender having a lower surface with a central through hole, and a capillary that may pass through the central hole and extend beyond the lower surface of the surface extender to define a nozzle. An electrospray liquid may be pumped through the capillary and may be emitted from the nozzle.

9 Claims, 8 Drawing Sheets

(56) References Cited

U.S. PATENT DOCUMENTS

| | | | |
|---|---|---|---|
| 9,050,611 B2 | 6/2015 | Pui et al. | |
| 2010/0264304 A1* | 10/2010 | Pablo | H01J 49/145 250/282 |
| 2014/0047905 A1* | 2/2014 | Tomany | B05B 5/0255 73/61.52 |

* cited by examiner

//  ENHANCING STABILITY AND THROUGHPUT OF AN ELECTROHYDRODYNAMIC SPRAY

CROSS REFERRENCE TO RELATED APPLICATION

This application claims the benefit of priority from U.S. Provisional Patent Application Ser. No. 62/304,246, filed on Mar. 6, 2016, and entitled "HIGH-FLOW STABLE ELECTROSPRAY," which is incorporated herein by reference in its entirety.

TECHNICAL FIELD

The present disclosure generally relates to the field of electrohydrodynamics, particularly to electrohydrodynamic spraying, and more particularly to methods and devices for enhancing the stability and throughput of a Taylor cone-jet formed during electrohydrodynamic spraying and electrospinning.

BACKGROUND

Electrospray is a liquid atomization method that may be utilized for a wide range of applications, from being used as an ionization source for mass spectrometry to generating nanometer sized droplets, or fibers in nanotechnology.

The electrospray emitter or nozzle may be a simple metallic capillary that may have a blunt tip. A liquid (i.e., electrospray medium) may be pumped with a flow rate of Q through the capillary, and a high voltage of V may be applied to the capillary. The capillary tip may be situated at a distance from a grounded electrode and the application of the voltage V between the capillary and the grounded electrode may lead to formation of an electrical field between the capillary tip and the grounded electrode. As the liquid leaves the tip of the capillary it may form a meniscus at the capillary tip. The meniscus may then deform into a conical shape under the electrical field. The conical shape is referred to as Taylor cone, from which a fine jet may erupt and subsequently this jet may break up either into fine droplets (i.e., electrospray) or extracted as fine fibers (i.e., electrospinning). This mode of operation, in which a Taylor cone and a jet is formed, may be referred to as a cone-jet mode.

An ideal electrospray emitter should allow for formation of a stable Taylor cone in order to ensure a robust operation of the electrospray system in a cone-jet mode. The emitter should allow for formation of a stable cone-jet for a large range of flow rates Q and voltages V. The ranges of Q and V in a Q-V space, for which a stable cone-jet may be formed, may be referred to as a stability margin or stability envelope for an electrospray system.

There is, therefore, a need in the art for an electrospray system with an emitter having a large stability margin. There is further a need in the art for an electrospray system capable of having a stable operation, i.e., the Taylor cone that may form in the operation will not frequently change its height, or detach from the jet under various external disturbances, such as small mechanical vibrations of the emitter, or fluctuations in ambient gas flow around the emitter or in the flow rate Q.

SUMMARY

In one general aspect, the present disclosure describes an emitting device for an electrospray system. The emitting device may include a surface extender having a lower surface with a central hole, and a capillary that may pass through the central hole and extend beyond the lower surface of the surface extender to define a nozzle. An electrospray liquid may be pumped through the capillary and may be emitted from the nozzle.

The above general aspect may include one or more of the following features. The lower surface of the surface extender may be a curved surface. In some implementations, the curved surface may be curved in the shape of a section of the exterior of a sphere, a paraboloid, or an ellipsoid.

In one implementation, the curved surface may be curved in the shape of a section of the exterior of a sphere with a diameter in a range of 2 to 9 times the outer diameter of the capillary.

In another implementation, the capillary may extend beyond the lower surface of the surface extender by a distance in a range of one tenth to one outer diameter of the capillary.

DETAILED DESCRIPTION

Figure 1:
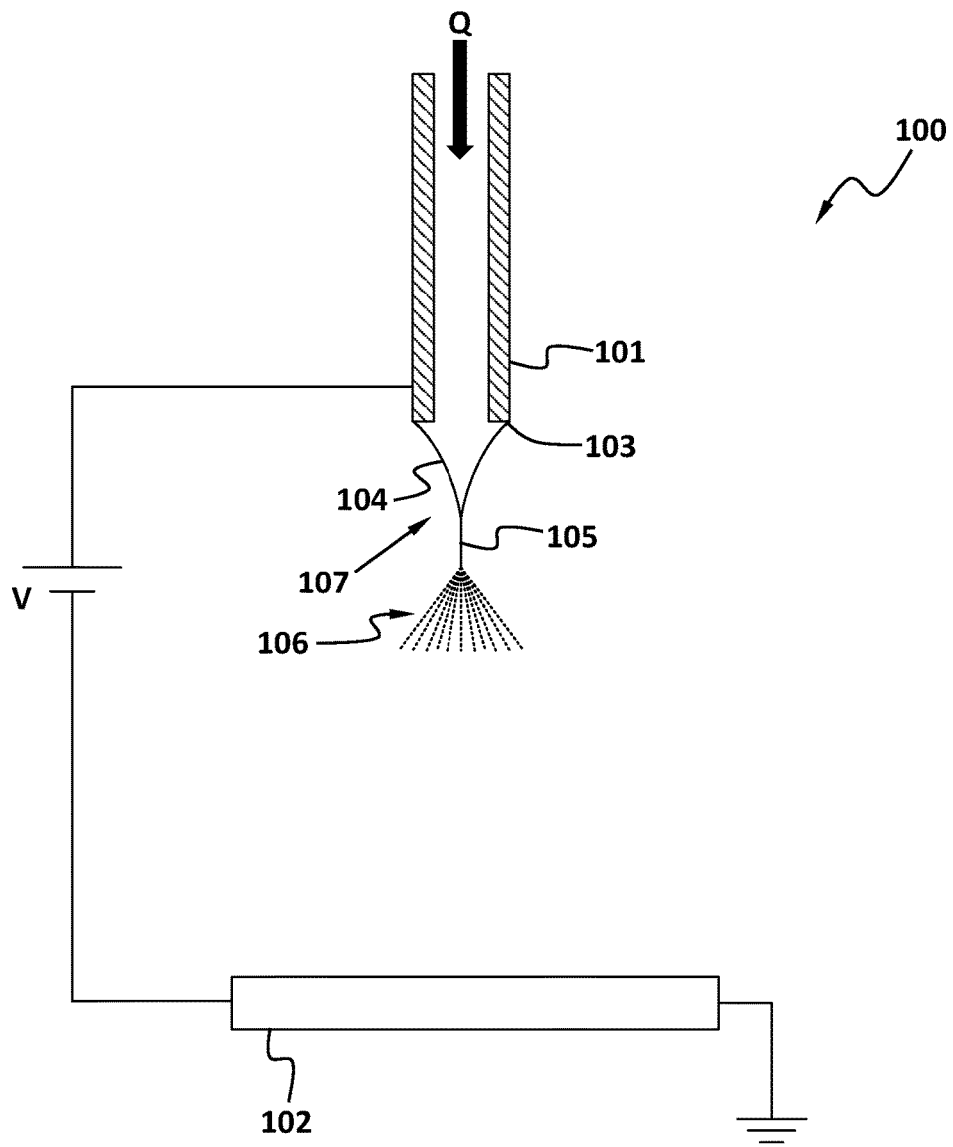
FIG. 1 is a schematic illustration of an exemplary electrospray apparatus.

FIG. 1A (related art) is a schematic illustration of an exemplary electrospray apparatus 100. An electrospray is produced when a sufficient electrical potential difference (designated by letter V) is applied between a conductive or partly conductive electrospray medium or fluid exiting a capillary 101 and a counter electrode 102 to generate a concentration of electric field lines emanating from the capillary tip 103. When a positive voltage V is applied to the capillary tip 103 relative to the counter electrode 102, the electric field causes positively-charged ions in the fluid to migrate to the surface of the fluid at the capillary tip 103. When a negative voltage V is applied to the capillary tip 103 relative to the counter electrode 102, the electric field causes negatively-charged ions in the fluid to migrate to the surface of the fluid at the capillary tip 103.

When the repulsion force of the solvated ions on the surface of the fluid counter balances the surface tension of the fluid being electro sprayed, a volume of the fluid is pulled into the shape of a cone, known as a Taylor cone 104, which extends from the tip of the capillary 101. A liquid jet 105 extends from the tip of the Taylor cone 104 and becomes unstable and generates charged-droplets 106. These small charged droplets 106 are drawn toward the counter electrode 102. The Taylor cone 104 and the liquid jet 105 may be referred to as a cone-jet structure 107.

The range of voltage V that may lead to a stable cone-jet structure 107 depends on the geometry of the capillary 101, electrodes configuration, flow rate Q, and liquid properties especially conductivity and surface tension. The limitation of the range of flow rates Q for which a stable cone-jet 107 may be formed reduces the benefit of electrospray in different applications. The maximum and minimum flow rates Q vary with liquid conductivity, and for every liquid with given properties there is a stability island in terms of flow rates Q and potential differences V in which the cone-jet 107 may be stable.

The stable cone-jet 107 may be confined between two boundaries at each flow rate Q, including: the upper voltage boundary between the cone-jet and multi-jet modes and the lower voltage boundary between the unstable spindle and the stable con-jet modes. The extension between the two boundaries reduces to zero with increasing the flow rate Q and a stable cone-jet 107 may only be achieved if the flow rate Q is sufficiently low.

Controlling the electric field near the capillary tip 103 may increase the voltage V range of cone-jet 107 stability and alter the angle of the spray plume, as well. Stability of the cone-jet 107 is crucial for combustion of liquid fuels in small scales, while in meso/micro scales it is important to produce very fine droplets 106 but with sufficiently large mass flow rates.

Disclosed herein is an exemplary emitting device that may be utilized for enhancing the stability margin of the cone-jet mode in an electrospray system, i.e., an emitter that may allow for producing a cone-jet that is stable for a wider range of flow rates Q and applied voltages V. The enhancement of the stability margin of the cone-jet mode may allow for designing electrospray systems with very high throughputs and thereby tackling one of the disadvantages of conventionalelectrospray systems.

In an aspect, the present disclosure describes an exemplary emitting device that may be utilized for an electrospray system. The emitting device may include a surface extender having a lower surface with a central through hole, and a capillary that may pass through the central hole. The capillary may extend beyond the lower surface of the surface extender to define a nozzle. An electrospray liquid may be pumped through the capillary and may be emitted from the nozzle.

Figure 2A:
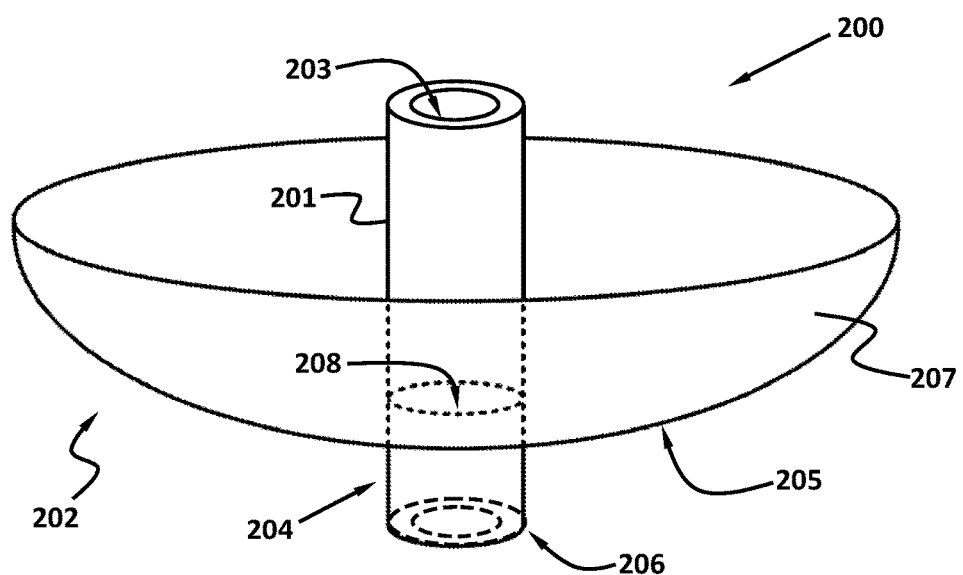
FIG. 2A illustrates an example of an emitting device, according to exemplary implementations of the present disclosure.
Figure 2B:
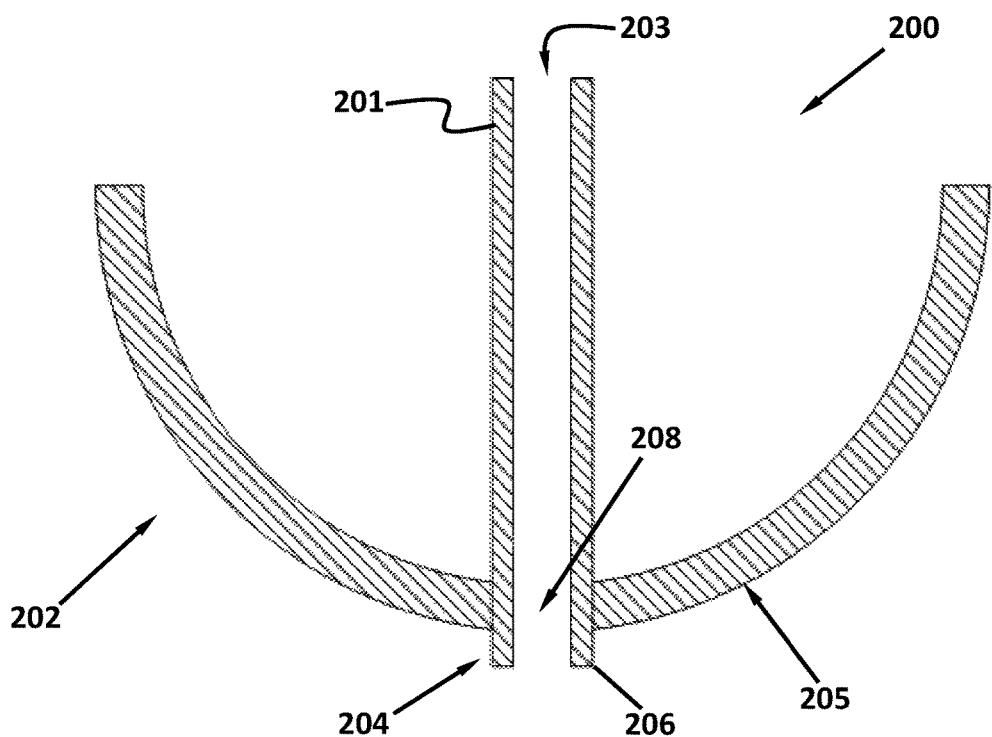
FIG. 2B is a sectional view of an example of an emitting device, according to exemplary implementations of the present disclosure.

FIG. 2A illustrates an example of emitting device 200, according to exemplary implementations of the present disclosure and FIG. 2B illustrates a sectional view of the emitting device 200.

Referring to FIGS. 2A and 2B, emitting device 200 may include capillary 201 and surface extender 202. Capillary 201 may have entrance orifice 203, through which the electrospray medium or fluid may be pumped; and nozzle 204 on extended ejection surface 205 that may be defined by surface extender 202. Capillary 201 may have a suitable cross-sectional shape, for example, circular or rectangular. Nozzle 204 may have an inner and an outer diameter. Nozzle 204 may be extended from ejection surface 205. Tip 206 of the nozzle may extend beyond ejection surface 205 with a predefined amount.

With further reference to FIGS. 2A and 2B, surface extender 202 may have lower curved surface 207 that may define ejection surface 205. Lower curved surface 207 may be curved in the shape of a section of the exterior of for example, a sphere, a paraboloid, an ellipsoid, etc. Surface extender 202 may have central hole 208 in the middle that may be configured to allow the passage of capillary 201. Capillary 201 may pass through central hole 208 and extend beyond surface 205 with a predefined amount. Surface extender 202 and capillary 201 may be integrally formed as a monolithic emitter.

Figure 4A:
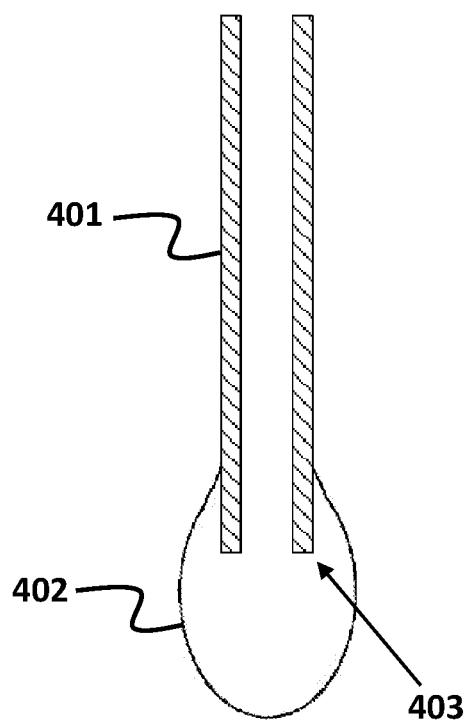
FIG. 4A shows a schematic of a droplet formed on the tip of an exemplary capillary emitter.
Figure 4B:
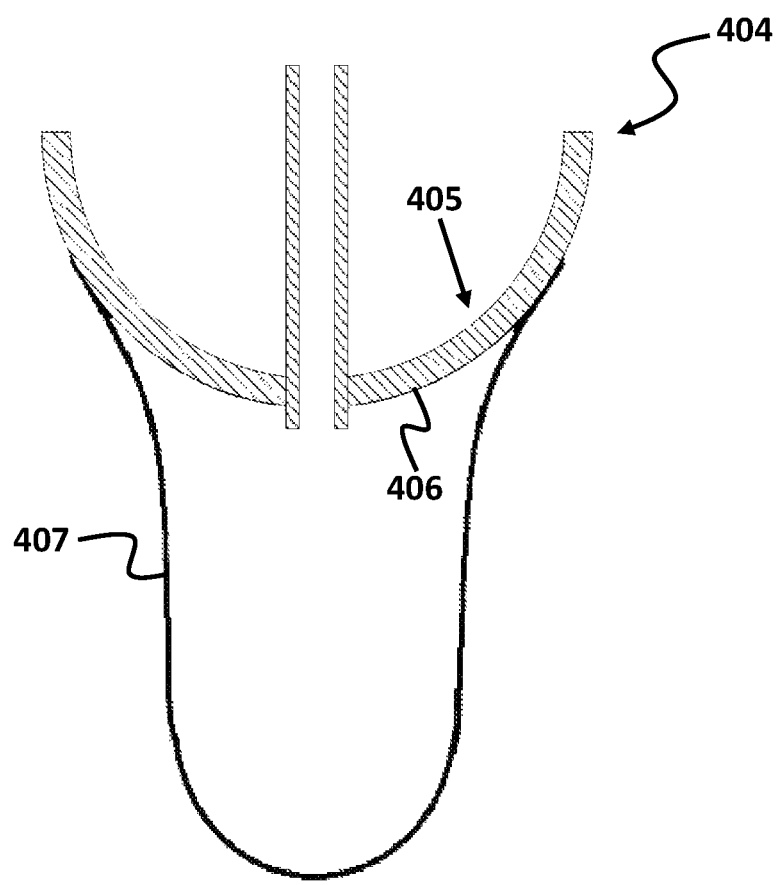
FIG. 4B shows a schematic of a droplet formed on the tip of an exemplary emitting device, according to one or more aspects of the present disclosure.

FIG. 4A shows droplet 402 formed on the tip of an exemplary capillary 401 and FIG. 4B shows a droplet formed on an exemplary emitting device with a surface extender. Referring to FIG. 4A, as the liquid leaves tip 403 of capillary 401, it may form a meniscus 402 at tip 403. Referring to FIG. 4B, when emitting device 404 with surface extender 405 is utilized, the liquid that leaves the tip of the capillary may interact with lower curved surface 406 of surface extender 405 and consequently a larger droplet 407 may be formed, compared to the droplet 402 formed on the tip of capillary emitter 401. Not bound by any particular theory, installing surface extender 405 may lead to an increase in the upward component of the surface tension that acts along the solid-liquid-vapor contact line on surface 406. The difference in the capillary pressure between the top and the bottom of the droplet which is due to the difference in gravitational potential energy, may lead to the formation of the larger droplet 407. Emitting device 404 with surface extender 405 may support a large liquid volume covering the nozzle tip. In embodiments, elements of FIG. 4 may be similar or have similar functionality of elements described with respect to FIG. 2 with similar names.

Figure 3:
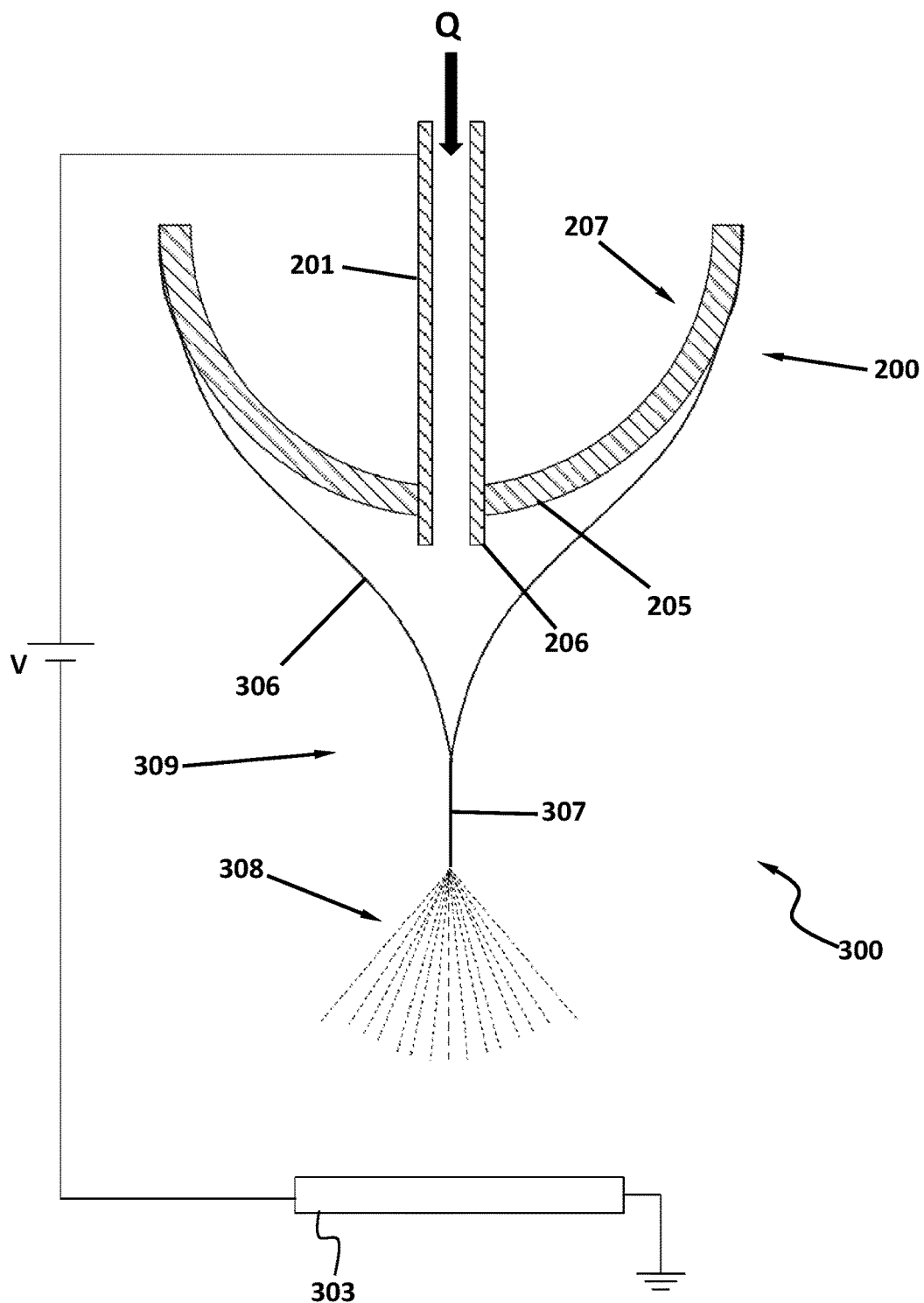
FIG. 3 is a schematic illustration of an exemplary electrospray apparatus utilizing an example of an emitting device, according to one or more aspects of the present disclosure.

FIG. 3 is a schematic illustration of an exemplary electrospray apparatus 300 that utilizes an example of an exemplary emitting device 200, according to one or more aspects of the present disclosure.

Referring to FIG. 3, an electrospray medium or liquid may be pumped through the capillary 201 with a flow rate of Q. As the liquid leaves the tip 206 of the capillary 201 it may form a relatively large meniscus at the capillary tip (as shown in FIG. 4B). The meniscus may then deform into a relatively large Taylor cone 306 under the electrical field that may be generated by a sufficient electrical potential difference (designated by letter V) applied between emitting device 200 and counter electrode 303. A liquid jet 307 may extend from the tip of the Taylor cone 306, and it may generate long fibers or become unstable and break up into charged-droplets (designated by reference number 308). These small charged droplets or fibers 308 may be drawn toward the counter electrode 303. The Taylor cone 306 and the liquid jet 307 may be referred to as a cone-jet structure 309. Utilizing the emitting device 200 of the present disclosure may lead to the formation of a stable cone-jet 309 for wider ranges of Q and V.

Referring to FIG. 2, according to some implementations, the distance between tip 206 of nozzle 204 and ejection surface 205 may be in a range of about one tenth of the outer diameter of nozzle 204 to about one outer diameter of nozzle 204. According to other exemplary implementations, curved surface 207 may be curved in the shape of a section of the exterior of a sphere with a diameter in a range of 8 to 9 times the outer diameter of the nozzle 204, alternatively the curved surface 207 may be curved in the shape of a section of the exterior of a paraboloid or an ellipsoid with a rim radius of about 5 to 10 times the outer diameter of the nozzle 204.

Figure 6:
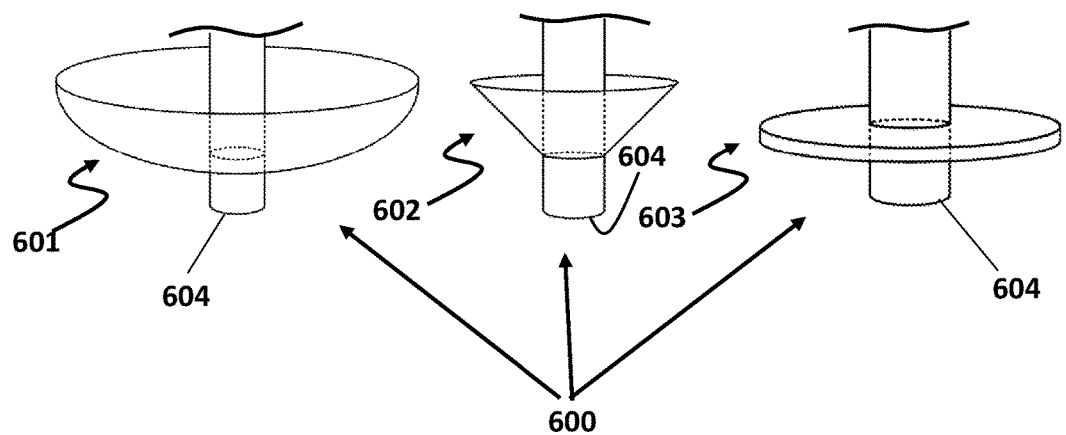
FIG. 6 illustrates different exemplary shapes of a surface extender, according to one or more exemplary implementations of the present disclosure.

Referring to FIG. 6, the emitting device 600 according to exemplary implementations of the present disclosure may utilize a surface extender with various shapes. The surface extender may be curved in the shape of a section of the exterior of a sphere, paraboloid, an ellipsoid, etc. (labeled as 601) or it may be a section of a cone (labeled as 602) or a flat surface (labeled as 603) that may be placed near a capillary emitter tip 604.

EXAMPLE 1

Stability Margin

In this example, emitting device 200 for an electrospray apparatus is described according to one exemplary implementation of the present disclosure. Referring to FIGS. 2A and 2B, emitting device 200 may include a surface extender 202 with a lower convex surface 207 that is in the shape of a section of the exterior of a sphere with a diameter of 6.2 mm. Surface extender 202 includes a central through hole 208 with a diameter of 0.7 mm that allows for passing capillary emitter 201 therethrough. Capillary emitter 201 has an inner diameter of 0.42 mm and an outer diameter of 0.7 mm. Capillary emitter 201 extends from surface 207 to form nozzle 204 with a length of 0.2 mm. Counter electrode 303 (an aluminum plate of 100×100×2 mm) was fixed at 35 mm from the tip of nozzle 204.

Referring to FIG. 3, in this example, emitting device 200 is utilized in an electrospray apparatus. A liquid with a flow rate of Q is pumped through capillary 201 and an electrical potential difference (designated by letter V) is applied between emitting device 200 and counter electrode 303. In order to compare the stability margin of emitting device 200 with a simple capillary emitter, a simple capillary emitter with an inner diameter of 0.42 mm and an outer diameter of 0.7 mm is also utilized in an electrospray apparatus under similar test conditions.

Ethanol as the electrospray liquid was supplied by a calibrated syringe pump while high voltages are applied between the nozzle and a plate. Applied voltages were measured using a high voltage probe and a digital multimeter with accuracy of 0.1%. The liquid meniscus were visualized by a high speed CCD camera (1000 FPS, AOS technology) and a digital camera (D7100, Nikon) combined with a lens (Micro-Nikkor 105 mm f/2.8 G from Nikon) and three automatic extension tube (12, 20, 36 mm, Kenko). The set provided a maximum magnification of 1.65 with a spatial resolution of 2.3 μm for diameter measurements. Jet diameters reported in this disclosure are averaged values of four images with a mean standard deviation of 3 μm. A white LED was used as an illuminating light source for capturing the images.

Figure 5:
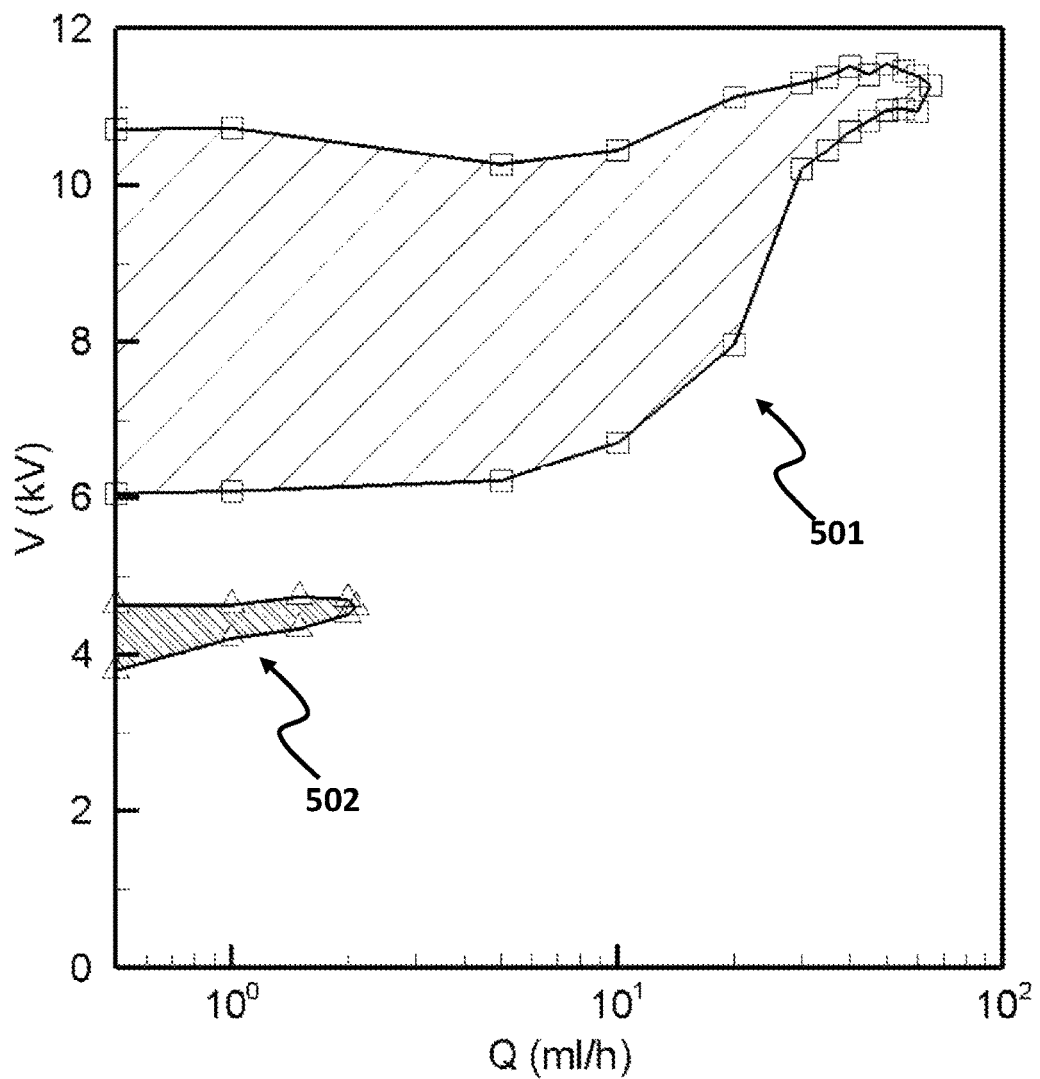
FIG. 5 shows stability margins of the Taylor cone-jet, as described in more detail in connection with exemplary implementations of the present disclosure.

FIG. 5 depicts stability margin 501 of the Taylor cone-jet formed at the tip of emitting device 200 and stability margin 502 of the Taylor cone-jet formed at the tip of a simple capillary emitter as described above. The applied voltage V is plotted versus the flow rate Q. Each flow rate Q is associated with a minimum voltage where the Taylor cone-jet mode is formed, and a maximum voltage beyond which the cone-jet is destabilized. Depending on the surrounding gas as well as the electrode configuration, the maximum voltage may be limited either by corona discharge or a transition to multi-jet mode. Referring to FIG. 5, for emitters with similar inner and outer diameters, stability margins 501 and 502 reveal that emitting device 200 may increase the maximum flow rate of the cone-jet mode to about 30 times greater compared to the maximum flow rate of a simple capillary emitter.

With further reference to FIG. 5, for example in a conventional simple emitter, the cone-jet voltage V range may be about 1 kV for low flow rates Q tending to decrease to zero at the maximum flow rate Q of about 2 ml/hr. At a constant flow rate Q, for instance, at 0.5 mL/hr a cone-jet structure could be observed between 3.7 kV to 4.6 kV for the conventional configuration. When emitting device 200 is utilized, at the same flow rate Q of about 0.5 mL/hr the cone-jet appears to be stable in a voltage V range between 6 kV and 10.6 kV.

The results in this particular example may indicate that at a constant flow rate Q, the voltage V range, for which a stable Taylor cone-jet is produced, may be about 2 to 4 times greater for emitting device 200 compared to a simple capillary emitter with similar capillary inner and outer diameters.

What is claimed is:

1. An emitting device for an electrospray system, the device comprising:
    a surface extender having a lower surface with a central hole thereon from a top-view, the surface extender having a circular shape from the top-view; and
    a capillary passing through the central hole and extending beyond the lower surface of the surface extender by a distance in a range of one tenth to one of an outer diameter of the capillary to define a nozzle,
    wherein:
    the capillary is configured to pass an electrospray liquid that is pumped through the capillary and to emit the electrospray liquid from the nozzle; and
    the lower surface of the surface extender is a curved surface from a cross-section view.

2. An emitting device for an electrospray system, the device comprising:
    a surface extender having a lower surface with a central hole thereon from a top-view, the surface extender having a circular shape from the top-view and the lower surface of the surface extender is a curved surface; and
    a capillary passing through the central hole and extending beyond the lower surface of the surface extender to define a nozzle,
    wherein the capillary is configured to pass an electrospray liquid that is pumped through the capillary and to emit the electrospray liquid from the nozzle.

3. The emitting device of claim 2, wherein the curved surface is curved in a shape of a section of an exterior of a sphere.

4. The emitting device of claim 3, wherein the sphere has a maximum diameter in a range of 2 to 9 times an outer diameter of the capillary.

5. The emitting device of claim 2, wherein the curved surface is curved in a shape of a section of an exterior of a paraboloid.

6. The emitting device of claim 5, wherein the paraboloid has a maximum diameter in a range of 5 to 10 times an outer diameter of the capillary.

7. The emitting device of claim 2, wherein the curved surface is curved in a shape of a section of an exterior of an ellipsoid.

8. The emitting device of claim 7, wherein the ellipsoid has a maximum diameter in a range of 5 to 10 times an outer diameter of the capillary.

9. The emitting device of claim 2, wherein the capillary extends beyond the lower surface of the surface extender by a distance in a range of one tenth to one of an outer diameter of the capillary.

\* \* \* \* \*